United States Patent
Yogi et al.

(10) Patent No.: US 9,459,271 B2
(45) Date of Patent: Oct. 4, 2016

(54) ANALYZER AND AUTOMATIC ANALYZER

(71) Applicant: Hitachi High-Technologies Corporation, Minato-ku, Tokyo (JP)

(72) Inventors: Takeshi Yogi, Tokyo (JP); Sakuichiro Adachi, Tokyo (JP); Hajime Yamazaki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/775,544

(22) PCT Filed: Mar. 31, 2014

(86) PCT No.: PCT/JP2014/059434
§ 371 (c)(1),
(2) Date: Sep. 11, 2015

(87) PCT Pub. No.: WO2014/163037
PCT Pub. Date: Oct. 9, 2014

(65) Prior Publication Data
US 2016/0025758 A1    Jan. 28, 2016

(30) Foreign Application Priority Data
Apr. 2, 2013  (JP) .................................. 2013-076932

(51) Int. Cl.
| | | |
|---|---|---|
| G01N 21/49 | (2006.01) | |
| G01N 35/02 | (2006.01) | |
| G01N 35/10 | (2006.01) | |
| G01N 21/25 | (2006.01) | |
| G01N 21/51 | (2006.01) | |
| G01N 21/82 | (2006.01) | |
| G01N 35/04 | (2006.01) | |

(52) U.S. Cl.
CPC .......... *G01N 35/025* (2013.01); *G01N 21/253* (2013.01); *G01N 21/49* (2013.01); *G01N 21/51* (2013.01); *G01N 21/82* (2013.01); *G01N 35/1002* (2013.01); *G01N 2021/825* (2013.01);
(Continued)

(58) Field of Classification Search
CPC ........................ G01N 21/49; G01N 2021/513
See application file for complete search history.

(56) References Cited

U.S. PATENT DOCUMENTS

| | | |
|---|---|---|
| 5,331,958 A | 7/1994 | Oppenheimer |
| 6,791,676 B1 | 9/2004 | Meller |

(Continued)

FOREIGN PATENT DOCUMENTS

| | | |
|---|---|---|
| EP | 0 411 620 A2 | 8/1990 |
| JP | 3-65654 A | 3/1991 |

(Continued)

OTHER PUBLICATIONS

English Translation of PCT/2014/059434.*

*Primary Examiner* — P. Kathryn Wright
(74) *Attorney, Agent, or Firm* — Miles & Stockbridge PC (57) ABSTRACT

To reduce the influence of air bubbles and dust in measuring scattered light beams on an automatic analyzer. A light source emits a light beam with a first wavelength 18a on a shorter wavelength side and a light beam with a second wavelength 18b on a longer wavelength side, and then, transmitted light beams 19a and 19b and scattered light beams 21a and 21b are received. Noise is estimated from the ratio between the intensities of the transmitted light beams with the first wavelength and the second wavelength and a change in the amount of the scattered light beam with the second wavelength. Then, the estimated noise is subtracted from a change in the amount of the scattered light beam with the first wavelength, so that noise due to air bubbles and dust is reduced.

12 Claims, 5 Drawing Sheets

(52) U.S. Cl.
CPC . *G01N 2035/0439* (2013.01); *G01N 2201/061* (2013.01); *G01N 2201/12* (2013.01)

(56) References Cited

U.S. PATENT DOCUMENTS

2013/0044325 A1    2/2013   Koyanagi
2013/0132022 A1    5/2013   Tamura et al.

FOREIGN PATENT DOCUMENTS

| JP | 6-38947 A | 2/1994 |
| JP | 2001-141654 A | 5/2001 |
| JP | 2003-80253 A | 3/2003 |
| JP | 2009-85708 A | 4/2009 |
| JP | 2011-237191 A | 11/2011 |
| JP | 2012-7921 A | 1/2012 |

* cited by examiner

ANALYZER AND AUTOMATIC ANALYZER

TECHNICAL FIELD

The present invention relates to a method and device for measuring scattered light beams generated by fine particle agglutination that uses an antigen-antibody reaction, and in particular, to a method for measuring scattered light beams on an automatic analyzer.

BACKGROUND ART

An automatic analyzer, which irradiates a reaction solution obtained by mixing a sample with a reagent, with a light beam from a light source, calculates absorbance from a change in the amount of a transmitted light beam with a specific wavelength, and thus quantitatively determines the concentration of a substance to be measured in the sample in accordance with the Lambert-Beer's law, is widely used. In such a device, a number of cells each holding a reaction solution are arranged on the circumference of a cell disc that repeatedly rotates and stops, and time-series data on the amount of light beams that have passed through the reaction solution in the cells is measured as reaction process data for about 10 minutes at intervals of about 15 seconds by a transmitted-light measuring unit located at a predetermined position while the cell disc rotates, so that absorbance is calculated from a change in the amount of the light beams, and the concentration of a substance to be measured is thus quantitatively determined.

Reactions that are measured with an automatic analyzer include two types: a color reaction of a substrate and an enzyme, and an immune reaction of an antigen and an antibody. An analysis that uses a color reaction is referred to as a biochemical analysis. Examples of test items of the biochemical analysis include LDH (lactate dehydrogenase), ALP (alkaline phosphatase), and AST (aspartate-oxoglutarate aminotransferase). An analysis that uses an immune reaction is referred to as an immune assay. Examples of test items of the immune assay include CRP (C-reactive protein), IgG (immunoglobulin), and RF (rheumatoid factor). Substances that are measured in an immune assay include test items that should be quantitatively determined in a low-concentration region in which the blood level is low. For such items, a latex immunoassay that uses as sensitizers latex particles, which have antibodies sensitized on (bound to) the surfaces thereof, is used. In the latex immunoassay, antigens, which are substances to be measured, in a sample are recognized by antibodies on the surfaces of latex particles contained in a reagent, and thus are bound thereto, so that the latex particles aggregate via the antigens, thus forming aggregates of latex particles. In the conventional automatic analyzer, a reaction solution in which such aggregates are dispersed is irradiated with light beams, and the amount of transmitted light beams that have passed through the aggregates of the latex particles without being scattered is measured. As the concentration of antigens is higher, the sizes of aggregates that are formed after a given period of time has elapsed becomes larger. Thus, the amount of scattered light beams becomes larger, while the amount of transmitted light beams becomes smaller. Therefore, the concentration of antigens can be quantitatively determined from the amount of light beams measured as the reaction process data.

In recent years, a further increase in sensitivity has been desired for latex immunoassays, and attempts have been made to measure not transmitted light beams but scattered light beams. For example, Patent Literature 1 discloses a system for separating transmitted light beams from scattered light beams using a diaphragm and measuring the transmitted light beams and the scattered light beams at the same time. Patent Literature 2 discloses a system for automatically calculating the difference between the intensities of detected light beams with two different wavelengths, and thus determining the analysis results. Other than automatic analyzers, Patent Literature 3 discloses a system for measuring exogenous macromolecules in the blood by determining the difference between a detection signal including a transmitted light beam and a scattered light beam at a wavelength of 670 nm and that at a wavelength of 940 nm.

CITATION LIST

Patent Literature

Patent Literature 1: JP 2001-141654 A
Patent Literature 2: JP H03-065654 A
Patent Literature 3: JP H06-038947 A

SUMMARY OF INVENTION

Technical Problem

With regard to automatic analyzers that use scattered light beams, there has been known no method that achieves high sensitivity by performing computation on pieces of reaction process data for a plurality of wavelengths so far. Although Patent Literature 1 discloses a configuration that achieves high sensitivity by measuring scattered light beams at the same time as transmitted light beams, it does not take a suitable configuration for an automatic analyzer into consideration. Patent Literature 2 achieves a reduction in noise for absorbance by performing computation on pieces of data for a plurality of wavelengths, but fails to disclose a method for performing computation on data on scattered light beams. Patent Literature 3 aims to measure exogenous macromolecules, but fails to disclose a method for acquiring reaction process data in a latex immunoassay.

When scattered light beams are measured to increase the sensitivity of a latex immunoassay, it is necessary to reduce noise generated by disturbance substances, such as dust or air bubbles. In particular, as measurement is performed using reaction process data, there is a problem in that signals may fluctuate due to air bubbles or dust that have grown or increased during a reaction process.

In addition, latex particles that are contained in a reagent for a latex immunoassay come in a wide range of densities in a reaction solution depending on the type of a reagent used, and thus, the influence of noise generated by disturbance substances, such as dust or air bubbles, would also differ depending on a reagent used. Thus, it is desired to use a noise canceling method that is not susceptible to the influence of the type of a reagent used, using the same optics.

Solution to Problem

In the present invention, a cell, which contains a reaction solution obtained by mixing a sample with a reagent, is irradiated with a light beam with a first wavelength and a light beam with a second wavelength, which is longer than the first wavelength, on the same optical path, and scattered light beams with the respective wavelengths are received. Then, a signal obtained by subtracting, from a signal representing a change in the amount of the scattered light beam with the first wavelength that has changed due to agglutination in the reaction solution, a signal, which has been obtained by multiplying a change in the amount of the scattered light beam with the second wavelength by a reagent coefficient that depends on the reagent, is determined so that the amount of a component in the sample is quantitatively determined on the basis of the determined signal.

Typically, the reagent contains latex particles that have diameters of 50 to 500 nm and have antibodies bound to the surfaces thereof, and a light beam with a wavelength in the range of 0.65 to 0.75 μm is used as the light beam with the first wavelength. It is possible to use as the reagent coefficient the ratio between the intensities of the light beam with the first wavelength and the light beam with the second wavelength that have passed through a cell, but it is also possible to store a reagent coefficient for each reagent in a storage unit in advance so that the reagent coefficient can be read and used as appropriate.

Advantageous Effects of Invention

According to the present invention, it is possible to cancel noise generated by disturbance substances in a latex immunoassay.

Other problems, configurations, and advantageous effects will become apparent from the following description of embodiments.

DESCRIPTION OF EMBODIMENTS

Hereinafter, embodiments of the present invention will be described with reference to the drawings.

Figure 1:
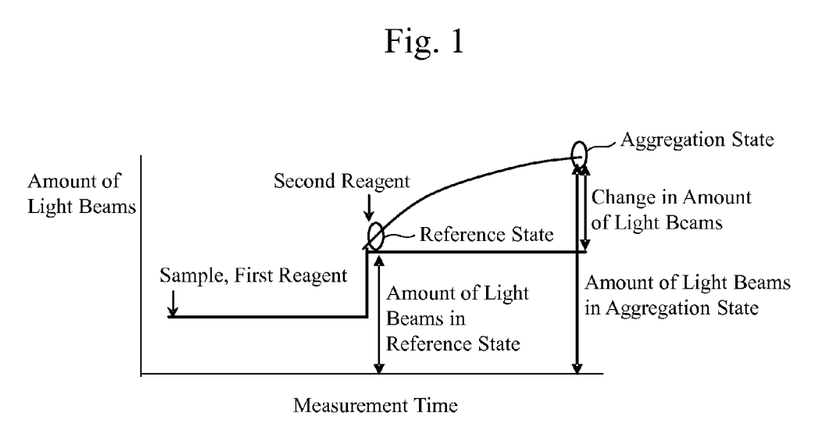
FIG. 1 is a schematic diagram showing scattered light beams measured in an antigen-antibody reaction with time.

FIG. 1 is a schematic diagram showing scattered light beams measured in an antigen-antibody reaction with time. On an automatic analyzer with a scattered-light measuring unit, a sample to which a first reagent has been added is first mixed with a second reagent in which latex particles with diameters of 50 to 500 nm are dispersed (i.e., reference state), and then, a change in the amount of scattered light beams or transmitted light beams after a given period of time has elapsed (i.e., aggregation state) is detected. Additionally, calibration data, which has been obtained by measuring a change in the amount of light beams using a known concentration of antigens, is prepared and compared with the aforementioned data on the change in the amount of scattered light beams or transmitted light beams, so that the concentration of antigens in the sample is calculated. In the present invention, calibration data is prepared by using a signal that has been obtained by performing computation (which is described below) on signals of scattered light beams with a first wavelength and a second wavelength. In addition, as a change in the amount of light beams is also proportional to the intensities of irradiation light beams, adjustment is performed so that the difference in the intensity between a light source with the first wavelength and a light source with the second wavelength is within 20%. Alternatively, the ratio between the intensities of the light sources with the first wavelength and the second wavelength is measured in advance, and the intensities of scattered light beams are divided using the ratio, so that variations in the intensities of scattered light beams due to variations in the intensities of light sources are suppressed. As a further alternative, it is also possible to, by pouring pure water into a cell, measuring the ratio between the intensities of transmitted light beams with the first wavelength and the second wavelength that have passed through the cell, and dividing the intensities of scattered light beams using the ratio, correct variations in the intensities of scattered light beams due to variations in the intensities of light sources.

Figure 2:
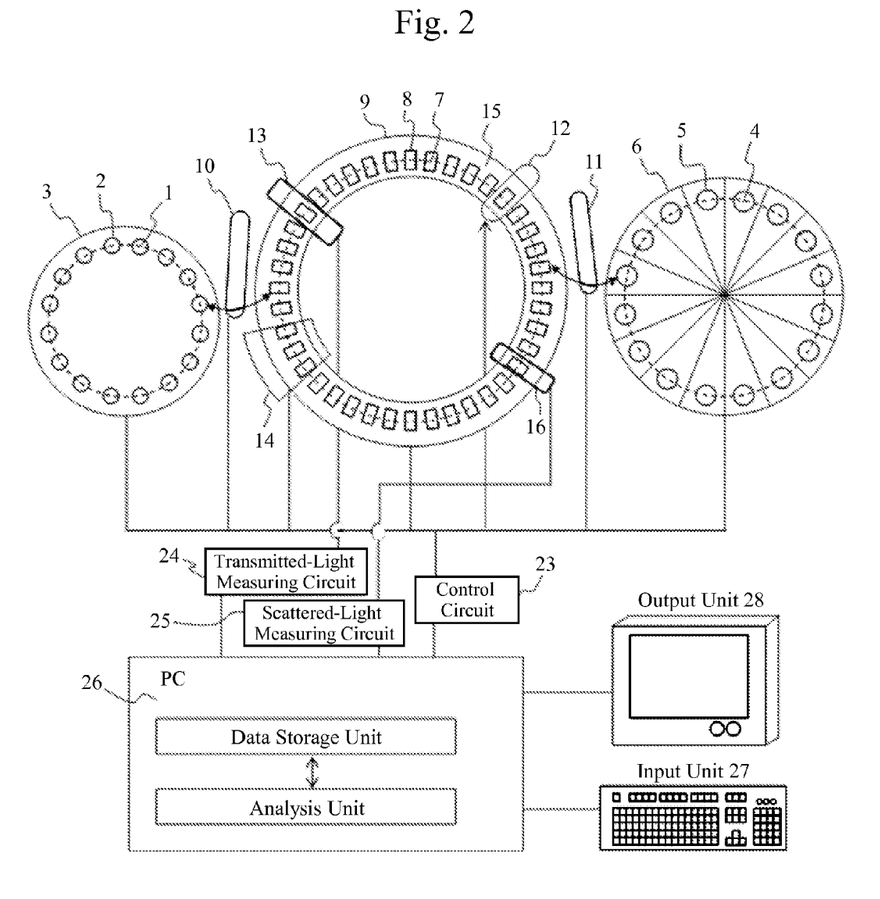
FIG. 2 is a schematic diagram showing an example of the entire configuration of an embodiment of an automatic analyzer.

FIG. 2 is a schematic diagram showing an example of the entire configuration of an embodiment of an automatic analyzer. The automatic analyzer in this embodiment can measure scattered light beams at the same time as transmitted light beams. The automatic analyzer in this embodiment includes three types of discs that are a sample disc 3, a reagent disc 6, and a cell disc 9, dispensing mechanisms for moving a sample and a reagent among such discs, a control circuit 23 for controlling them, a transmitted-light measuring circuit 24, a scattered-light measuring circuit 25, a data processing unit 26, such as a PC (computer), for processing measured data, an input unit 27 that is an interface for inputting data to or outputting data from the data processing unit 26, and an output unit 28. The data processing unit 26 includes an analysis unit for analyzing data and a data storage unit for storing control data, measurement data, data used for analyses, analysis result data, and the like.

A plurality of sample cups 2 each containing a sample 1 are disposed on the circumference of the sample disc 3. A plurality of reagent bottles 5 each containing a reagent 4 are disposed on the reagent disc 6. A plurality of cells 8, each of which contains a reaction solution 7 obtained by mixing the sample 1 with the reagent 4 therein, are arranged on the circumference of the cell disc 9. A sample dispensing mechanism 10 moves the sample 1 from the sample cup 2 to the cell 8 by a given amount. A reagent dispensing mechanism 11 moves the reagent 4 from the reagent bottle 5 to the cell 8 by a given amount. An agitating unit 12 agitates and mixes the sample 1 and the reagent 4 in the cell 8. A washing unit 14 discharges the reaction solution 7 from the cell 8 in which an analysis process has terminated and thereafter washes the cell 8. A next sample 1 is dispensed again from the sample dispensing mechanism 10 into the cell 8 that has been washed, while a new reagent 4 is dispensed from the reagent dispensing mechanism 11 into the cell 8 so as to be used for another reaction process. The cells 8 are immersed in a constant-temperature fluid 15 in a thermostatic bath with controlled temperature and flow rate. Therefore, the cells 8 and the reaction solutions 7 therein are moved while being kept at a constant temperature. For the constant-temperature fluid 15, water is used, for example, and the temperature of the constant-temperature fluid is adjusted in the range of 37±0.1° C. by the control circuit 23. A transmitted-light measuring unit 13 and a scattered-light measuring unit 16 are provided on parts of the circumference of the reaction disc 9.

The transmitted-light measuring unit 13 can have a configuration in which, for example, the cell 8 is irradiated with light beams emitted from a halogen lamp light source, and transmitted light beams that have passed through the cell 8 are split by diffraction gratings, and the split light beams are received by a photodiode array. Examples of the wavelengths of light beams that are received by the photodiode array include 340 nm, 405 nm, 450 nm, 480 nm, 505 nm, 546 nm, 570 nm, 600 nm, 660 nm, 700 nm, 750 nm, and 800 nm. Data on the amount of transmitted light beams that are received by the photodiode array is sent to the data storage unit in the PC via the transmitted-light measuring circuit 24.

Figure 3:
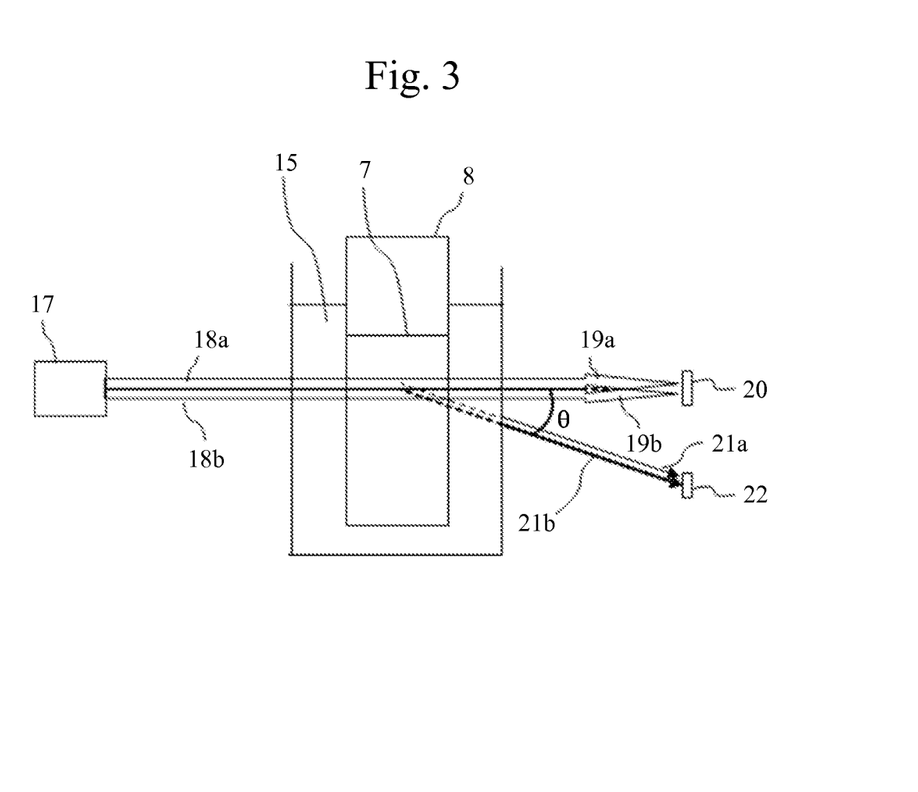
FIG. 3 is a schematic diagram of a scattered-light measuring unit.

FIG. 3 is a schematic diagram of the scattered-light measuring unit 16. As a light source, a LED light source unit can be used, for example. Irradiation light beams 18a and 18b from a LED light source unit 17 are caused to irradiate the cell 8 that is moving, and transmitted light beams 19a and 19b are received by a transmitted-light receiving unit 20, while scattered light beams 21a and 21b are received by a scattered-light receiving unit 22. The irradiation light beams 18a and 18b, the transmitted light beams 19a and 19b, and the scattered light beams 21a and 21b are light beams with different wavelengths, and pass through the same spatial region. The wavelengths of scattered light beams to be measured may be wavelengths included in the range of 650 to 750 nm or wavelengths longer than such wavelengths, desirably a wavelength of greater than or equal to 900 nm.

Figure 4:
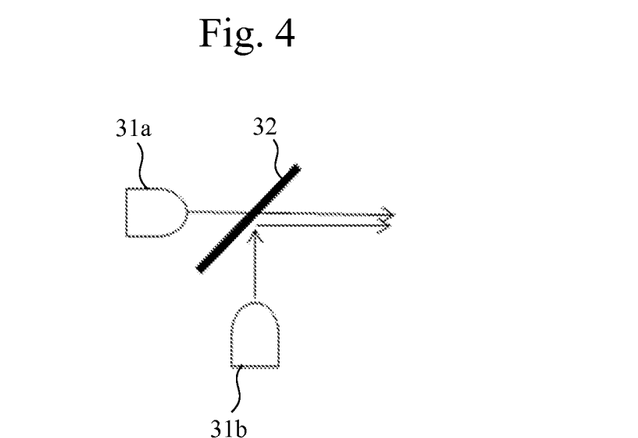
FIG. 4 is a schematic diagram of a light source unit.

FIG. 4 is a schematic diagram of the LED light source unit 17. Light beams emitted from the LED light source unit 17 include light beams with at least two wavelengths. For example, a light beam with a wavelength of 700 nm from a LED 31a and a light beam with a wavelength of 950 nm from a LED 31b are combined by a half mirror 32 and are adjusted to be oriented along the same optical axis as shown in FIG. 4, and the combined beams are emitted as the irradiation light beams 18. Although the LEDs 31a and 31b each having a single wavelength are used as the light sources in this embodiment, it is also possible to use a white LED, a laser, a Xenon lamp, or a halogen lamp. It is also possible to use a light source with a configuration in which a fluorescent material is used so that a light beam with a first wavelength is emitted from a LED light source, and a light beam with a second wavelength is emitted using the light beam with the first wavelength via the fluorescent material. For example, when a halogen lamp that generates white light beams is used as the light source, it is possible to split the light beams at a light receiving unit, and measure the amount of light beams with a wavelength of 700 nm and the amount of light beams with a wavelength of 950 nm.

The scattered-light receiving unit 22 measures the scattered light beams 21a and 21b in the direction away from the optical axis by an angle of θ in the air. The angle θ may be any angle in the range of 15 to 35°. In this embodiment, θ=20°. The scattered-light receiving unit 22 is disposed in a plane that is generally perpendicular to the direction in which the cell 8 is moved by rotation of the cell disc 9. Herein, as the reference position of the angle θ, the center of the length for which a light beam passes in the cell 8 is set as the starting point.

Figure 5:
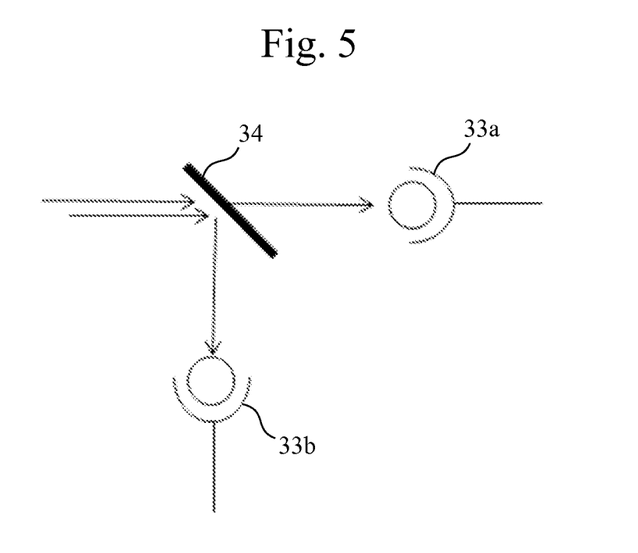
FIG. 5 is a schematic diagram of a scattered-light receiving unit.

FIG. 5 is a schematic diagram of the scattered-light receiving unit 22. The scattered-light receiving unit 22 has a function of splitting light beams, and separates scattered light beams into a light beam with a first wavelength of 700 nm and a light beam with a second wavelength of 950 nm using a dichroic mirror 34, for example, so that the respective light beams are received by photodiodes 33a and 33b.

Although light beams are split into light beams with two wavelengths by the scattered-light receiving unit 22 in this embodiment, it is also possible to use white light beams of a halogen lamp or the like as irradiation light beams, and use a beam splitter unit that incorporates diffraction gratings as the scattered-light receiving unit 22.

Quantitative determination of the concentration of a substance to be measured in the sample 1 is performed in accordance with the following procedures. First, a given amount of the sample 1 in the sample cup 2 is dispensed into the cell 8 by the sample dispensing mechanism 10. Next, a given amount of the reagent 4 in the reagent bottle 5 is dispensed into the cell 8 by the reagent dispensing mechanism 11. During dispensing, the sample disc 3, the reagent disc 6, and the cell disc 9 are rotation-driven by their respective drive units under the control of the control circuit 23, and thus move at the dispensing timings of the sample cup 2, the reagent bottle 5, and the cell 8, respectively. Next, the sample 1 and the reagent 4 dispensed into the cell 8 are agitated by the agitating unit 12 to obtain the reaction solution 7. Transmitted light beams and scattered light beams from the reaction solution 7 are measured each time the beams pass through the measurement positions in the transmitted-light measuring unit 13 and the scattered-light measuring unit 16, respectively, while the cell disc 9 rotates, and are sequentially accumulated as reaction process data in the data storage unit of the data processing unit 26 from the transmitted-light measuring circuit 24 and the scattered-light measuring circuit 25. Measurement is performed for a given period of time, for example, for about 10 minutes. Then, the inside of the cell 8 is washed by the washing unit 14, and a next test item is analyzed. During the process, another reagent 4 is dispensed into the cell 8 by the reagent dispensing mechanism 11 as needed, so that agitation is performed by the agitating unit 12 and measurement is performed for another given period of time. Accordingly, pieces of reaction process data on the reaction solution 7 at given time intervals are stored in the data storage unit.

A change in the amount of light beams due to a reaction that has occurred for a given period of time is determined by the analysis unit from the stored reaction process data of the scattered-light measuring unit, so that results of quantitative determination are calculated on the basis of calibration curve data held in the data storage unit in advance, and are displayed by the output unit. Data that is necessary for control of each unit and analysis is input to the data storage unit of the data processing unit 26 from the input unit 27. A variety of pieces of data, results, and alarm in the storage unit are output from the output unit 28 via display and the like.

In this embodiment, a reaction solution is irradiated with light beams with at least two wavelengths on the same optical path, and scattered light beams generated from the reaction solution are received, and then, computation is performed on the scattered light beam signals with two wavelengths, using a reagent coefficient that is determined for each reagent, whereby a change in the amount of light beams (noise) due to disturbance substances is reduced. In particular, a value, which has been obtained by multiplying a scattered light beam signal of a light beam with a longer wavelength of the two wavelengths by a reagent coefficient, is subtracted from a scattered light beam signal of a light beam with a shorter wavelength, so that noise is reduced.

Hereinafter, a more specific description will be made. Adjustment is performed so that the intensities of the light beams with the first wavelength and the second wavelength that irradiate a cell become equal. Then, the reagent coefficient k is determined as follows from the intensities $I_{t1}$ and $I_{t2}$ of transmitted light beams with the first wavelength and the second wavelength that have passed through the reaction solution immediately after a reaction started.

$$k=I_{t1}/I_{t2}$$

Next, computed reaction process data: $I_{s\text{-}cal}(t)=I_{s1}(t)-k\times I_{s2}(t)$ is obtained using the amounts of scattered light beams with the first wavelength and the second wavelength $I_{s1}(t)$ and $I_{s2}(t)$ that have changed during the reaction and the reagent coefficient k, so that the amount of a component in the sample is quantitatively determined using the computed reaction process data.

Although a method for determining the reagent coefficient k from the intensities of transmitted light beams that have passed through a reaction solution immediately after a reaction started is shown herein, the reagent coefficient k may also be set for each reagent used before measurement is started.

Figure 6:
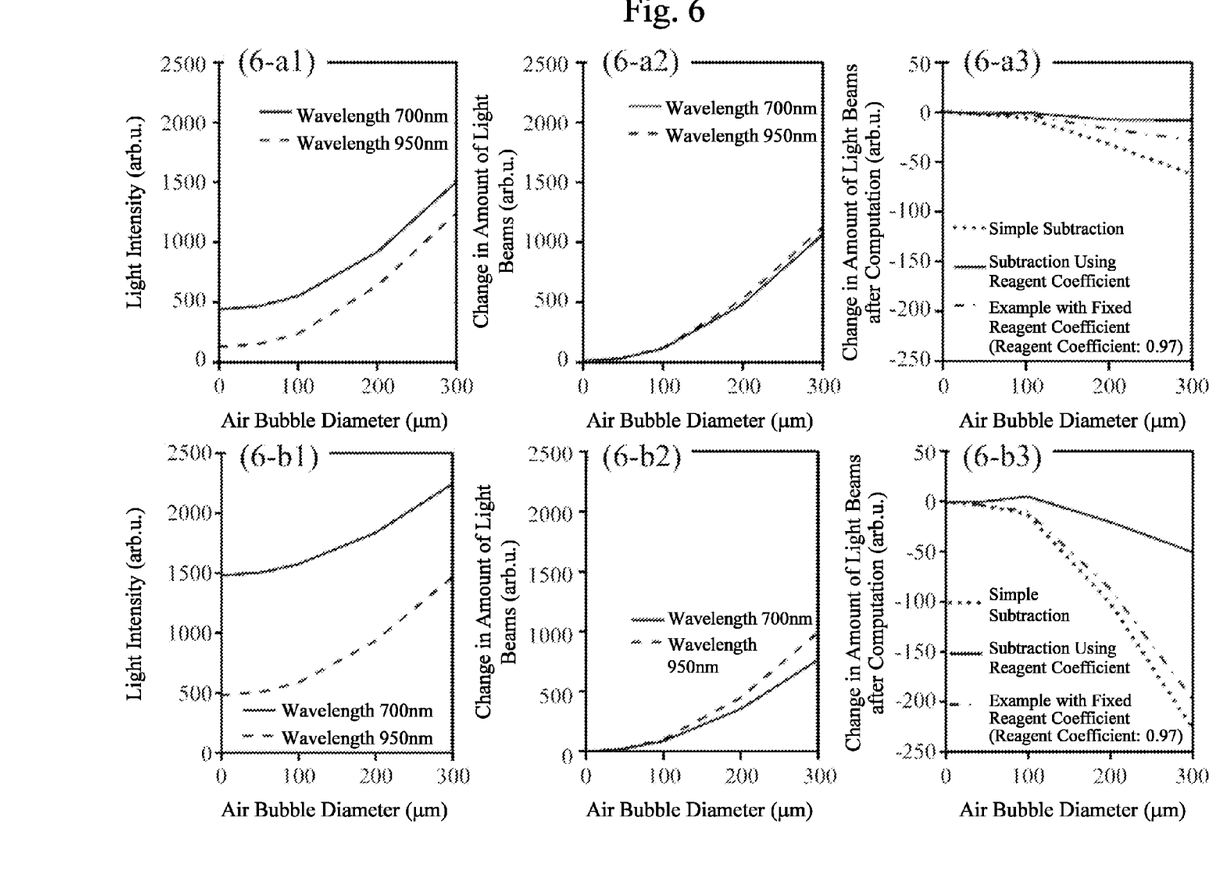
FIG. 6 are diagrams showing the influence of noise due to air bubbles and the results of computation.

FIG. 6 are diagrams showing the influence of noise due to air bubbles and the results of computation. FIGS. (6-a1) and (6-b1) show simulation results of the intensities of scattered light beams with a first wavelength of 700 nm and a second wavelength of 950 nm when air bubbles that are disturbance substances have stuck to the cell wall and have grown. Simulation was performed by disposing air bubbles on the inner wall of a cell, which contains a reaction solution and has an optical path length of 5 mm, at the center of the optical axes of the irradiation light beams, and computing scattered light beams in the direction of θ=20° from the irradiation light beams.

In this simulation, it is supposed that air bubbles are located at the cell wall on the light receiving unit side. However, similar results are obtained even when air bubbles have stuck to the cell wall on the irradiation light beam side. That is, when air bubbles have stuck to the cell wall on the light receiving unit side, irradiation light beams that have passed through the reaction solution and have attenuated are scattered by the air bubbles, while when air bubbles have stuck to the cell wall on the irradiation light beam side, irradiation light beams are first scatted by the air bubbles, and then pass through the reaction solution and attenuate. Herein, the proportion light beams that encounter air bubbles and thus are scattered and the proportion of light beams that pass through the reaction solution and attenuate do not depend on the wall to which the air bubbles have stuck. Consequently, the intensities of scattered light beams that are generated by air bubbles and enter the light receiving unit become almost the same independently of the cell wall.

Air bubbles and dust in the reaction solution are sufficiently larger than the wavelength used for measurement, and the proportion of air bubbles that are included in the range of air bubble diameters shown in FIG. 6 is high. Herein, FIGS. (6-a1) and (6-b1) show data in a reaction solution that contains latex particles with a diameter of 300 nm and an absorbance of 0.08 (abs) and 0.30 (abs), respectively, at a wavelength of 700 nm (or an absorbance of 0.03 (abs) and 0.13 (abs), respectively, at a wavelength of 950 nm). FIGS. (6-a2) and (6-b2) are diagrams of changes in the amounts of scattered light beams generated by air bubbles with respective diameters when the air bubbles grow and thus have increased diameters, with reference to the intensity of scattered light beams when the air bubble diameter is 0 μm, that is, when there is no air bubble.

Hereinafter, the reagent coefficient k is determined from the ratio between the intensities of transmitted light beams $I_t$ (700 nm) and $I_t$ (950 nm) that have passed through a reaction solution immediately after a reaction started. When the intensities $I_0$ of irradiation light beams with respective wavelengths are adjusted at the same level, the intensities of the transmitted light beams are as follows at an optical path length of 5 mm in FIG. (6-a1) (i.e., 0.08(abs) at a wavelength of 700 nm):

$$I_t(700\text{ nm})=10^{-(0.08/2)}\times I_0, \, I_t(950\text{ nm})=10^{-(0.03/2)}\times I_0,$$

and the reagent coefficient k is as follows:

$$k=I_t(700\text{ nm})/I_t(950\text{ nm})=10^{-(0.08/2)}/10^{-(0.03/2)}\cong 0.95.$$

Similarly, the reagent coefficient k is 0.82 in FIG. (6-b1) (i.e., 0.30(abs) at a wavelength of 700 nm).

As the intensities of transmitted light beams that have passed through a reaction solution immediately after a reaction started, it is also possible to use values measured with the transmitted-light measuring unit. In addition, the reagent coefficient may be set for each reagent before measurement is started, and stored in the data storage unit, and then extracted for use.

FIGS. 6-a3) and (6-b3) show examples of the results of subtraction: $\{I_{s\text{-}cal}=I_s(700\text{ nm})-k\times I_s(950\text{ nm})\}$ performed by using changes in the amounts of scattered light beams $I_s(700\text{ nm})$ and $I_s(950\text{ nm})$ at wavelengths of 700 nm and 950 nm, respectively, and the reagent coefficient k; the results of simple subtraction $\{I_s(700\text{ nm})-I_s(950\text{ nm})\}$; and the results of subtraction performed by fixing the reagent coefficient to k=0.97.

From FIGS. (6-a2) and (6-b2), it is found that a change in the amount of scattered light beams generated by air bubbles is larger at a wavelength of 950 nm than at a wavelength of 700 nm, and the higher the absorbance of the reagent, the grater the difference. This is because, as the particle diameter of a reagent is typically in the range of 50 to 500 nm, the absorbance of the reagent differs between cases where the wavelength is short and long, and thus, as a transmitted light beam that irradiates disturbance substances, such as dust or air bubbles, is smaller at a shorter wavelength, a change in the amount of light beams due to disturbance substances is smaller at a shorter wavelength.

Therefore, when a simple subtraction is performed between two wavelengths or when a subtraction is performed with a fixed reagent coefficient, the width of subtraction between the two wavelengths becomes large depending on a reagent used. However, if a reagent coefficient, which reflects the intensities of transmitted light beams that have passed through a reaction solution immediately after a reaction started, is used, it becomes possible to suppress a change in the amount of light beams due to disturbance substances down to ¼ or less as compared to a case where simple subtraction is performed (see FIGS. (6-a3) and (6-b3)).

Meanwhile, in contrast with the wavelength-dependence against disturbance substances, a change in the amount of light beams due to a reaction is greater at a shorter wavelength in the wavelength range of greater than or equal to visible light. Therefore, using the result of the aforementioned subtraction can suppress influence due to disturbance substances and determine a change in the amount of light beams due to a reaction.

In the automatic analyzer in this embodiment, the data processing unit 26 performs computation $\{I_{s\text{-}cal}=I_s(700\text{ nm})-k\times I_s(950\text{ nm})\}$ using the reagent coefficient k on the basis of changes in the amounts of scattered light beams $I_s(700\text{ nm})$ and $I_s(950\text{ nm})$ at a wavelength of 700 nm and a wavelength of 950 nm, respectively, and then, the result of the computation $I_{s\text{-}cal}$ is checked against calibration curve data held in the data storage unit so that the amount of a component in the sample is quantitatively determined.

Accordingly, it is possible to reduce influence of air bubbles and dust that have stuck to the cell wall and thus perform a quantitative analysis with high accuracy.

It should be noted that the present invention is not limited to the aforementioned embodiments, and includes a variety of variations. For example, although the aforementioned embodiments have been described in detail to clearly illustrate the present invention, the present invention need not include all of the structures described in the embodiments. It is possible to replace a part of a structure of an embodiment with a structure of another embodiment. In addition, it is also possible to add, to a structure of an embodiment, a structure of another embodiment. Further, it is also possible to, for a part of a structure of each embodiment, add, remove, or substitute a structure of another embodiment. In addition, the drawings that are shown are only those that are considered to be necessary for the description, and not all of structural portions or functions that are necessary for a product are shown.

REFERENCE SIGNS LIST

1 Sample
2 Sample cup
3 Sample disc
4 Reagent
5 Reagent bottle
6 Reagent disc
7 Reaction solution
8 Cell
9 Cell disc
10 Sample dispensing mechanism
11 Reagent dispensing mechanism
12 Agitating unit
13 Transmitted-light measuring unit
14 Washing unit
15 Constant-temperature fluid
16 Scatted-light measuring unit
17 LED light source unit
18a,18b Irradiation light beams
19a,19b Transmitted light beams
20 Transmitted-light receiving unit
21a,21b Scattered light beams
22 Scattered-light receiving unit
23 Control circuit
24 Transmitted-light measuring circuit
25 Scattered-light measuring circuit
26 Data processing unit
27 Input unit
28 Output unit
31a,31b LED
32 Half mirror
33a,33b Photodiode
34 Dichroic mirror

The invention claimed is:

1. An analyzer comprising:
a cell containing a reaction solution obtained by mixing of a sample with a reagent;
a light source unit configured to irradiate the cell with a light beam with a first wavelength and a light beam with a second wavelength on the same optical path, the second wavelength being longer than the first wavelength;
a light receiving unit configured to receive a scattered light beam with the first wavelength and a scattered light beam with the second wavelength, the scattered light beams having been generated by interaction with the reaction solution in the cell; and
a data processing unit configured to determine a signal by subtracting, from a signal representing a change in an amount of the scattered light beam with the first wavelength that has changed due to agglutination in the reaction solution, a signal that has been obtained by multiplying a change in an amount of the scattered light beam with the second wavelength by a reagent coefficient that depends on the reagent, and quantitatively determine an amount of a component in the sample on the basis of the determined signal,
wherein a ratio between intensities of the light beam with the first wavelength and the light beam with the second wavelength that have passed through the cell is used as the reagent coefficient.

2. The analyzer according to claim 1, wherein
the reagent contains particles with diameters of 50 to 500 nm, and
a light beam with a wavelength in a range of 0.65 to 0.75 μm is used as the light beam with the first wavelength.

3. The analyzer according to claim 1, wherein a ratio between intensities of the light beam with the first wavelength and the light beam with the second wavelength that irradiate the cell is adjusted to be within a predetermined error range.

4. The analyzer according to claim 1, further comprising a storage unit that stores the reagent coefficient for each reagent, wherein the data processing unit is configured to read and use the reagent coefficient stored in the storage unit.

5. The analyzer according to claim 1, wherein intensities of the light beam with the first wavelength and the light beam with the second wavelength are normalized using intensities of transmitted light beams for when the cell contains pure water.

6. The analyzer according to claim 1, wherein the reagent coefficient is determined using intensities of transmitted light beams that have passed through the reaction solution immediately after the agglutination started.

7. An automatic analyzer comprising:
a sample disc that has disposed thereon a plurality of sample cups each containing a sample, the sample disc being configured to be rotation-driven;
a reagent disc that has disposed thereon a plurality of reagent bottles each containing a reagent, the reagent disc being configured to be rotation-driven;
a cell disc that has disposed thereon a plurality of cells each containing a reaction solution, the cell disc being configured to be rotation-driven;
a sample dispensing mechanism configured to dispense a sample into one of the cells on the cell disc from one of the sample cups on the sample disc;
a reagent dispending mechanism configured to dispense a reagent into one of the cells on the cell disc from one of the reagent bottles on the reagent disc;
a measuring unit configured to perform optical measurement on the cell on the cell disc that is rotation-driven, the cell containing a reaction solution obtained by mixing the sample with the reagent; and
a data processing unit configured to process data measured with the measuring unit,
wherein
the measuring unit includes
a light source unit configured to irradiate the cell with a light beam with a first wavelength and a second light beam with a second wavelength on the same optical path, the second wavelength being longer than the first wavelength, and a light receiving unit configured to receive a scattered light beam with the first wavelength and a scattered light beam with the second wavelength, the scattered light beams having been generated by interaction with the reaction solution in the cell, and the data processing unit is configured to determine a signal by subtracting, from a signal representing a change in an amount of the scattered light beam with the first wavelength that has changed due to agglutination in the reaction solution, a signal that has been obtained by multiplying a change in an amount of the scattered light beam with the second wavelength by a reagent coefficient that depends on the reagent, and quantitatively determine an amount of a component in the sample on the basis of the determined signal, wherein a ratio between intensities of the light beam with the first wavelength and the light beam with the second wavelength that have passed through the cell is used as the reagent coefficient.

8. The automatic analyzer according to claim 7, wherein the reagent contains particles with diameters of 50 to 500 nm, and a light beam with a wavelength in a range of 0.65 to 0.75 µm is used as the light beam with the first wavelength.

9. The automatic analyzer according to claim 7, wherein a ratio between intensities of the light beam with the first wavelength and the light beam with the second wavelength that irradiate the cell is adjusted to be within a predetermined error range.

10. The automatic analyzer according to claim 7, further comprising a storage unit that stores the reagent coefficient for each reagent, wherein the data processing unit is configured to read and use the reagent coefficient stored in the storage unit.

11. The automatic analyzer according to claim 7, wherein intensities of the light beam with the first wavelength and the light beam with the second wavelength are normalized using intensities of transmitted light beams for when the cell contains pure water.

12. The automatic analyzer according to claim 7, wherein the reagent coefficient is determined using intensities of transmitted light beams that have passed through the reaction solution immediately after the agglutination started.

* * * * *